(12) United States Patent
Ohnishi et al.

(10) Patent No.: US 6,736,967 B2
(45) Date of Patent: May 18, 2004

(54) SEPARATING AGENT FOR ENANTIOMERIC ISOMERS

(75) Inventors: Atsushi Ohnishi, Ibaraki (JP); Shinsuke Suzuki, Hyogo (JP); Masato Sakai, Kanagawa (JP)

(73) Assignee: Daicel Chemical Industries, Ltd., Osaka (JP)

( * ) Notice: Subject to any disclaimer, the term of this patent is extended or adjusted under 35 U.S.C. 154(b) by 69 days.

(21) Appl. No.: 10/162,128

(22) Filed: Jun. 4, 2002

(65) Prior Publication Data

US 2003/0010696 A1 Jan. 16, 2003

(30) Foreign Application Priority Data

Jun. 7, 2001 (JP) ..................................... 2001-172053

(51) Int. Cl.$^7$ ............................................. B01D 15/08
(52) U.S. Cl. ............................ 210/198.2; 210/502.1; 210/635; 210/656; 502/404
(58) Field of Search .......................... 210/635, 656, 210/198.2, 502.1; 502/404

(56) References Cited

U.S. PATENT DOCUMENTS

| | | | | |
|---|---|---|---|---|
| 5,030,354 | A | | 7/1991 | Miwa et al. ................ 210/635 |
| 5,202,433 | A | * | 4/1993 | Okamoto et al. ........... 540/200 |
| 5,489,387 | A | * | 2/1996 | Namikoshi et al. ......... 210/635 |
| 6,217,769 | B1 | * | 4/2001 | Okamoto et al. ........... 210/635 |
| 6,444,814 | B1 | * | 9/2002 | Ikeda et al. ................ 544/192 |
| 6,605,717 | B2 | * | 8/2003 | Ikeda et al. ................ 544/192 |

FOREIGN PATENT DOCUMENTS

| | | | |
|---|---|---|---|
| JP | 57-150432 | 9/1982 | ............ 210/198.2 |
| JP | 63-307829 | 12/1988 | ............ 210/198.2 |
| JP | 2-289601 | 11/1990 | ............ 210/198.2 |

OTHER PUBLICATIONS

Article, Reprinted from the Journal of the American Chemical Society, 1984, vol. 106, No. 18; *Useful Chiral Packing Materials for High–Performance Liquid Chromatographic Resolution of Enantiomers: Phenylcarbamates of Polysaccharides Coated on Silica Gel*; Yoshio Okamoto, et al; pp. 5357–5359; (3 pages).

Article, Reprinted from Pharm Tech Japan, vol. 12, No. 1 (1996), *Separation of Chiral Compounds*; Daicel Chemical, Shigeo Makino, pp. 43–52 (10 pages).

* cited by examiner

*Primary Examiner*—Ernest G. Therkorn
(74) *Attorney, Agent, or Firm*—Flynn, Thiel, Boutell & Tanis, P.C.

(57) ABSTRACT

A separating agent for enantiomeric isomers has an enantiomerically active polymer compound supported thereon. The polymer compound has an exothermic peak before a decomposition temperature of the polymer compound supported is reached in a differential calorimetric curve obtained in a process of temperature elevation in differential scanning calorimetry (DSC) on the separating agent. Also, disclosed is a method of evaluating asymmetry recognition ability of a separating agent for enantiomeric isomers. The method includes performing the differential scanning calorimetry (DSC) of a separating agent for enantiomeric isomers having supported thereon an enantiomerically active polymer compound to obtain a differential calorimetric curve in a process of temperature elevation therein, and observing presence or absence of an exothermic peak of the polymer compound in the differential calorimetric curve before a decomposition temperature of the supported polymer compound is reached. The evaluation method provides a simpler method for the evaluation of asymmetry recognition ability and thus provides a separating agent for enantiomeric isomers having higher ability of recognizing asymmetry.

5 Claims, 3 Drawing Sheets

SEPARATING AGENT FOR ENANTIOMERIC ISOMERS

FIELD OF THE INVENTION

The present invention relates to a separating agent for enantiomeric isomers, in particular, a separating agent used for separating enantiomeric isomers in liquid chromatography. More particularly, the present invention relates to a separating agent for enantiomeric isomers that can enantiomerically resolve a broad range of chiral compounds with high separation factors in the analysis of pharmaceuticals, foods, agricultural chemicals, fragrants and the like and a method of evaluating the ability of recognizing asymmetry of such a separating agent.

PRIOR ARTS

Many organic compounds have isomers that have the same physical and chemical properties, such as boiling point, melting point and solubility but show a difference in a physiological activity, i.e., enantiomeric isomers. This difference in physiological activity between the isomers is attributable to the following. In most cases, proteins and carbohydrates that compose a living body of a living organism are composed only of the one of enantiomeric isomers so that they show a difference in the manner of action to the other kinds of enantiomeric isomers, resulting in a difference in the physiological activity. This can be compared to a difference in easiness (difference in physiological activity) of wearing of a glove for left hand (i.e., a living organism as an enantiomerically active substance) between the right hand and the left hand (respective enantiomeric isomers that act).

In particular, in the field of pharmaceutical preparations, in many cases, there are significant differences in medical property and toxicity between the two enantiomeric isomers. Therefore, in the Guideline for the Production of Pharmaceuticals, the Ministry of Health, Labor and Welfare describes a policy for making a sharp distinction between enantiomeric isomers saying "when the drug of interest is a racemic modification, it is desirable to preliminarily study absorption, distribution, metabolism and excretion kinetics of each enantiomeric isomer."

Since enantiomeric isomers have completely the same physical and chemical properties, such as boiling point, melting point, and solubility as previously stated, they cannot be analyzed by ordinary separation means. For this reason, extensive studies have been made on techniques for separating enantiomeric isomers that analyze a wide variety of enantiomeric isomers conveniently and with high precision. As a result, as an analytical technique that meets these requirements, an enantiomeric resolution method by high performance liquid chromatography (HPLC), in particular an enantiomeric resolution method by using a chiral column for HPLC has been developed. The chiral column referred to herein uses an asymmetry recognition agent itself or a chiral stationary phase composed of an asymmetry recognition agent supported on a suitable carrier.

For example, enantiomerically active poly (triphenylmethyl methacrylate) (cf., JP 57-150432 A), cellulose or amylose derivatives (Y. Okamoto, M. Kawashima and K. Hatada, J. Am. Chem. Soc., 106, 5357, 1984), ovomucoid, which is a protein (JP 63-307829 A) and the like have been developed.

It has been known that among many chiral stationary phases for HPLC, an enantiomeric resolution column having supported cellulose or amylose derivative on silica gel has high asymmetry recognition ability to an extremely wide variety of compounds. Furthermore, in recent years, studies on a liquid chromatographic fractionation method for fractionating enantiomerically active substances on an industrial scale including a chiral stationary phase for HPLC and a simulated moving bed method, which is a continuous liquid chromatographic fractionation method in combination have been developed (Pharm Tech. Japan, 12, 43 (1996)).

For example, enantiomerically active poly (triphenylmethyl methacrylate) (cf., JP 57-150432 A), cellulose or amylose derivatives (Y. Okamoto, M. Kawashima and K. Hatada, J. Am. Chem. Soc., 106, 5357, 1984), ovomucoid, which is a protein (JP 63-307829 A) and the like have been developed.

It has been known that among many chiral stationary phases for HPLC, an enantiomeric resolution column having supported cellulose or amylose derivative on silica gel has high asymmetry recognition ability to an extremely wide variety of compounds. Furthermore, in recent years, studies on a liquid chromatographic fractionation method for fractionating enantiomerically active substances on an industrial scale including a chiral stationary phase for HPLC and a simulated moving bed method, which is a continuous liquid chromatographic fractionation method in combination have been developed (Pharm Tech. Japan, 12, 43 (1996)).

In the case of chiral stationary phase for HPLC used as analysis means, complete separation of two enantiomeric isomer peaks in a short analysis time gives a full satisfaction. However, in order to further increase fractionation productivity, a liquid chromatographic fractionation method as production means has been required to not only completely separate a compound as a target of fractionation but also further separate two enantiomeric isomer peaks of the target compound; that is, a chiral stationary phase having a value of separation factor $\alpha$ as high as possible has been desired.

Under the circumstances, various contrivances have been made to more fully develop the asymmetry recognition ability of the chiral stationary phase including an enantiomerically active polymer compound such as, for example, a polysaccharide derivative as an asymmetry recognition agent to obtain a further increased value of separation factor $\alpha$. Under the present conditions, however, there are no evaluation methods for high asymmetry recognition ability other than those that use an HPLC measurement in reality. Accordingly, a simpler and easier method of evaluating asymmetry recognition ability has been demanded.

JP-A 2-289601 discloses a separating agent comprising a polysaccharide derivative having —CO—NHR for OH.

SUMMARY OF THE INVENTION

The present invention has been achieved under the above-mentioned circumstances. That is, an object of the present invention is to provide a simpler and easier method of evaluating asymmetry recognition ability. Another object of the present invention is to provide a separating agent for enantiomeric isomers having higher asymmetry recognition ability by using the evaluation method.

As a result of extensive studies for achieving the above-mentioned objects, the inventors of the present invention have now found that those separating agents that cause polymer compounds which have been supported therein to exhibit exothermic peaks before the polymer compounds reach their decomposition temperatures in a differential thermal calorimetric curve obtained in a heat elevation process in differential scanning calorimetry (DSC) have high values of separation factors α of enantiomeric isomers, thereby achieving the present invention.

Therefore, the present invention provides a separating agent for enantiomeric isomers, comprising an enantiomerically active polymer compound supported thereon, wherein the polymer compound has an exothermic peak before a decomposition temperature of the polymer compound supported is reached in a differential calorimetric curve obtained in a process of temperature elevation in differential scanning calorimetry (DSC) on the separating agent.

It then provides a method of evaluating asymmetry recognition ability of a separating agent for enantiomeric isomers, comprising: performing a differential scanning calorimetry (DSC) of the separating agent for enantiomeric isomers having supported thereon an enantiomerically active polymer compound to obtain a differential calorimetric curve in a process of temperature elevation therein; and observing presence or absence of an exothermic peak of the polymer compound in the differential calorimetric curve before a decomposition temperature of the supported polymer compound is reached.

DETAILED DESCRIPTION OF THE INVENTION

Hereinafter, the present invention will be described in detail by embodiments. However, the present invention is not limited thereto.

The enantiomerically active polymer compounds used in the present invention include polysaccharide derivatives, enantiomerically active polyamides, enantiomerically active polyesters, enantiomerically active polyamino acids, enantiomerically active polyethers, polymers having bound thereto enantiomerically active compounds, proteins, and modified proteins and complexes of these. In particular, polysaccharide derivatives or complexes thereof are suitably used.

The polysaccharide derivatives used in the present invention can be obtained by reacting a polysaccharide with a compound having a functional group that is reactive with the hydroxyl groups of the polysaccharide.

The polysaccharide may be any polysaccharide, being a synthetic or natural one or a modified natural one. The polysaccharide has preferably a high regularity in the manner of binding between saccharides. Examples of the polysaccharide include β-1,4-glucan (cellulose), α-1,4-glucan (amylose or amylopectin), α-1,6-glucan (dextran), β-1,6-glucan (pustulan), β-1,3-glucan (for example, curdlan, schizophyllan, etc.), α-1,3-glucan, β-1,2-glucan (crown gall polysaccharide), β-1,4-galactan, β-1,4-mannan, α-1,6-mannan, β-1,2-fructan (inulin), β-2,6-fructan (levan), β-1,4-xylan, β-1,3-xylan, β-1,4-chitosan, α-1,4-N-acetylchitosan (chitin), pullulan, agarose and alginic acid. Also, starches containing amylose are included therein. Among these polysaccharides, it is preferable to use cellulose, amylose, β-1,4-xylan, β-1,4-chitosan, chitin, β-1,4-mannan, inulin, curdlan, etc. which can be easily obtained as highly pure polysaccharides, still preferably cellulose and amylose.

It is preferable that such a polysaccharide has a number-average degree of polymerization (i.e., the average number of pyranose or furanose rings per molecule) of at least 5, still preferably at least 10. From the viewpoint of handling properties, it is preferable that the number-average degree of polymerization thereof is not more than 1,000, though the upper limit thereof is not particularly defined.

The compounds having functional groups capable of reacting with the hydroxyl groups of the polysaccharide may be isocyanic acid derivatives, carboxylic acids, esters, acid halides, acid amides, halides, aldehydes, alcohols and any other compounds having leaving groups. As these compounds, use can be made of aliphatic, alicyclic, aromatic and heteroaromatic ones. Particularly preferable examples of the polysaccharide derivative to be used in the present invention include ester and carbamate derivatives of polysaccharides having at least 0.1 ester or urethane bond per glucose unit, more preferably ester and carbamate derivatives having an asymmetic center.

The enantiomerically active polymer compound is supported on the carrier preferably in an amount of from 1 to 100% by weight, more preferably from 5 to 60% by weight, and particularly preferably from 15 to 40% by weight, based on the carrier.

The carrier referred to herein includes organic porous substrates and inorganic porous ones, preferably inorganic porous ones. Appropriate examples of the organic porous substrates include polymers comprising polystyrene, polyacrylamide, polyacrylate, etc. Appropriate examples of the inorganic porous substrates include silica, alumina, magnesia, glass, kaolin, titanium oxide, silicates and hydroxyapatite. Silica gel may be cited as a particularly preferable carrier. The particle diameter of the silica gel is from 0.1 μm to 10 mm, preferably from 1 μm to 300 μm, and more preferably from 5 μm to 50 μm and the average pore size thereof is from 10 angstroms to 100 μm, preferably from 50 angstroms to 50,000 angstroms. When silica gel is employed as the carrier, it is preferable to preliminarily surface-coat the silica gel so as to exterminate the effects of the silanol remaining therein, though a non-surface-treated one may be used without any problem.

In the separating agent having supported thereon the enantiomerically active polymer compound of the present invention, the polymer compound may be applied and supported on the carrier through physical adsorption, or may be more firmly immobilized thereto by further forming chemical bonds. These chemical bonds may be formed by, for example, chemical bonds between the carrier and the coated polymer compound, chemical bonds between the polymer compound molecules on the carrier, chemical bonds formed by using a third component, or chemical bonds formed by reactions caused by irradiation of light, radiation such as γ-ray, or electromagnetic wave such as micro wave onto the polymer compound on the carrier, or by radical reactions. Furthermore, enantiomerically active polymer compounds as asymmetry recognition agents and enantiomerically inactive polymer compounds may be simultaneously supported on the carrier.

The separating agent for enantiomeric isomers of the present invention is characterized in that when differential scanning calorimetry (DSC) is performed, the polymer compound has an exothermic peak in a differential calorimetric curve obtained in a first heat elevation process before its decomposition temperature is reached; separating agents having such exothermic peaks can have higher asymmetry recognition ability.

It is preferred that DSC measurements are performed in a nitrogen atmosphere. The rate of heat elevation is not particularly limited. It is preferred to perform the DSC measurements at a rate of 0.5 to 100° C./min, more preferably 5 to 50° C./min. The temperatures at which the DSC measurements are started are not particularly limited. However, it is preferred that the measurements are started at lower temperature than room temperature.

In the DSC measurements, the separating agent containing the polymer compound of the invention, having the exothermic peak(s), may be considered to have an unstable structure in part or on a whole. The method of producing the separating agent containing the polymer compound of the invention is not in particular specified. Conditions of preparation that will influence formation of the unstable structure include, in general for example, heating of the polymer compound, rapid cooling, addition of a plasticizer or another additive and modification caused by introducing a bulky substituent into the polymer compound.

The separating agent of the invention can be obtained by dissolving an enantiomerically active polymer compound in a solvent to obtain a polymer dope, supporting it on a carrier and distilling the solvent out. After the distillation, the product may be heated and then cooled. The product is determined with a differential scanning calorimetry (DSC) to select a polymer compound having an exothermic peak before the decomposition temperature of the polymer compound supported has been reached in the differential calorimetric curve obtained in temperature elevation procedures with the differential scanning calorimetry (DSC) on the separating agent. The supporting step may be carried out by mixing or coating. The distillation may be carried out by heating at a reduced pressure. The supporting step and the distillating step may be repeated.

The separating agent of the invention may be obtained with changed distillating period in time, which may depend on the selected solvent or the distillating temperature.

The solvent to use for supporting the enantiomerically active polymer compounds on the carrier includes any solvent for the used polysaccharide derivative, for example, ketone solvents, ester solvents, ether solvents, amide solvents, imide solvents, hydrocarbon solvents, acid solvents, amine solvents, halogenated solvents, alcohol solvents and nitrile solvents. A single or plural mixed solvents may be used.

The temperature for supporting the enantiomerically active polymer compound on the carrier may be 20° C. to 80° C.

The distilling period in time after having supported the enantiomerically active polymer compound on the carrier may depend on the solvent used for the supporting step.

The heating treatment may be carried out at any temperature that is not more than the decomposition temperature of the supported enantiomerically active polymer compound, for example preferably at 100° C. or lower. The cooling step may be effected rapidly or slowly. The slow cooling may be carried out by allowing the product to stand at a room temperature after the heating. The rapid cooling may be carried out with ice bathing or in a liquid at 0° C. or lower such as dry ice-ethanol, dry ice-methanol and liquid nitrogen.

The separating agent of the invention may be used in enantiomeric resolution for example, in chromatography such as gas chromatography, liquid chromatography, thin layer chromatography, super critical chromatography and capillary electrophoresis and then membrane separation. In particular it may be preferably used as a chiral immobilized (stationary) phase of the liquid chromatography. it may be also used for enantiomeric resolution by continuous-wise liquid chromatography such as the simulated moving bed.

A third additive may be used at the supporting step of the enantiomerically active polymer compound on the carrier, for example, any compound not bleeding out during separating use, preferably a polymer such as polystyrene, polycaprolactam, AS resin, poly-methyl methacrylate, polyacetal and polycarbonate.

EXAMPLES

Hereinafter, the present invention will be described in more detail by way of examples. However, the present invention should not be construed as being limited to these examples.

Example 1

Production of an Amylose Tris[(S)-phenylethyl Carbamate]-Supported Separating Agent for Enantiomeric Isomers having an Exothermic Peak before Reaching a Decomposition Temperature (1) Surface Treatment of Silica Gel A porous silica gel (particle diameter: 20 μm) was subjected to aminopropylsilane (APS) treatment in a conventional manner by reacting with 3-aminopropyltriethoxysilane. The obtained APS-treated silica gel was reacted with isocyanate to obtain carbamoyl-surface-treated silica gel.

(2) Synthesis of Amylose Tris[(S)-phenylethyl Carbamate]

In a nitrogen atmosphere, 109 g of (S)-phenylethyl isocyanate (2 equivalents based on hydroxyl group of amylose) was added to a mixture of 20 g of amylose and 500 ml of dry pyridine and the obtained mixture was heated under stirring at a pyridine reflux temperature for 24 hours. After cooling, the reaction mixture was poured into 5.0 liters of methanol stirred at room temperature over 10 minutes. Then, the resultant mixture was stirred for 30 minutes, and left to stand for 30 minutes. After, the supernatant was removed by decantation. The solid of amylose tris[(S)-phenylethyl carbamate] finally precipitated was taken up by filtration through a glass filter and washed with 300 ml of methanol three times on the glass filter, followed by vacuum drying (60° C., 5 hr). As a result, 69.2 g (93%) of yellowish white solid was obtained.

(3) Supporting of Amylose Tris[(S)-phenylethyl Carbamate] on Silica Gel 10 g of the amylose tris[(S)-phenylethyl carbamate] obtained in the step (2) was dissolved in a mixed solution composed of 95 ml of tetrahydrofuran (THF) and 5 ml of N,N-dimethylacetamide. Half of the resultant polymer dope was applied uniformly onto 40 g of the silica gel described in the step (1). After the completion of the application, THF was distilled off under reduced pressure with heating over 60 minutes or more. The remaining half of the polymer dope was uniformly applied to the silica gel in the same manner as described above and THF was distilled off under reduced pressure in the same manner as the first time to obtain the objective amylose tris[(S)-phenylethyl carbamate]-supported separating agent.

(4) Differential Scanning Calorimetry (DSC) of the Separating Agent Prepared in the Step (3)

Figure 1:
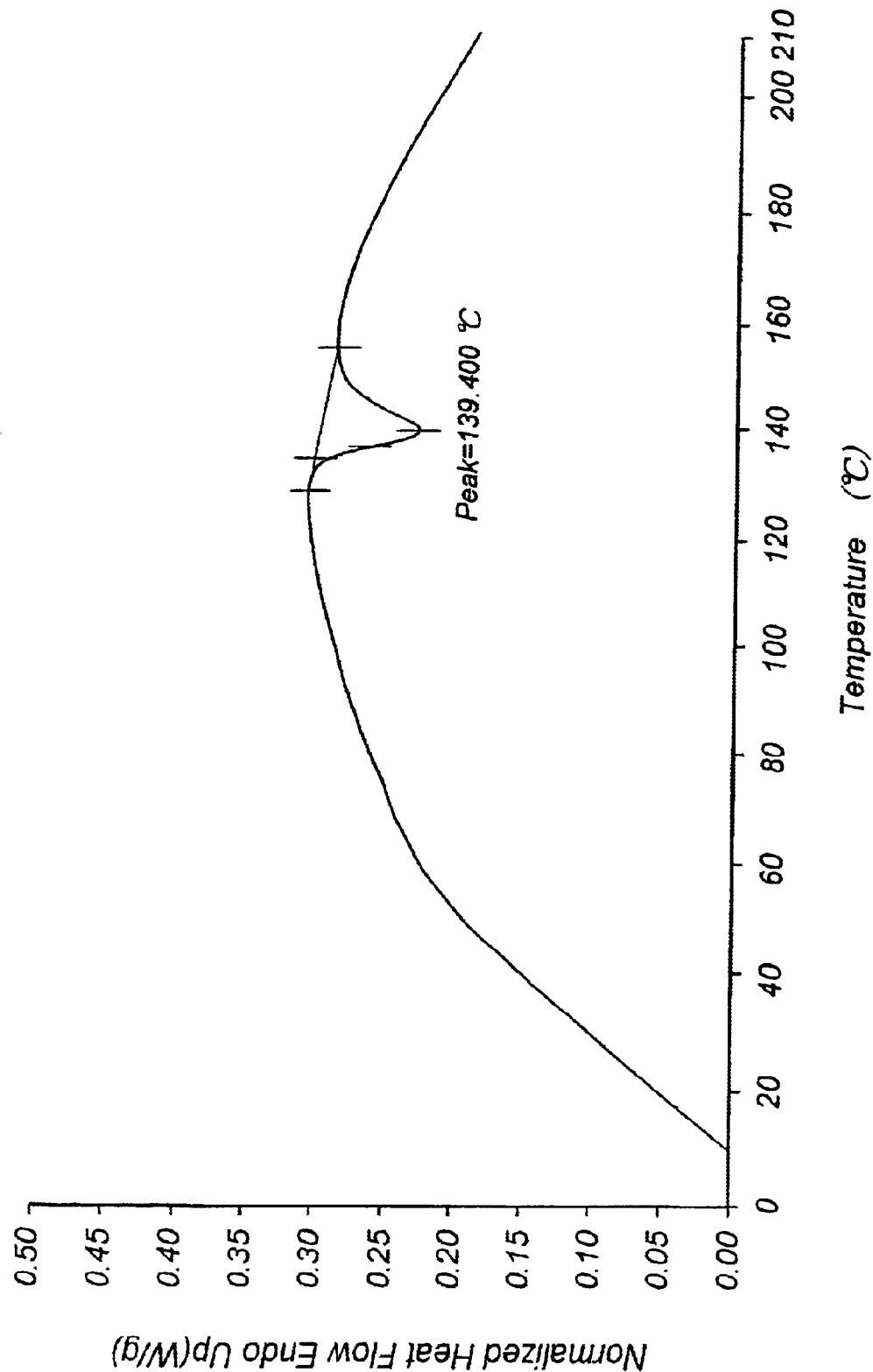
FIG. 1 is a chart illustrating the measurement results of DSC as measured in the step (4) in Example 1 of the present invention.

For measurements, DSC-7 manufactured by Perkin-Elmer Corporation was used. The separating agent was subjected to vacuum drying at 50° C. for 2 hours before the measurement and 5 mg of the separating agent charged in an aluminum-made cell having a diameter of 7 mm was used as a sample. The measurement was performed in a nitrogen atmosphere by holding the sample at 0° C. for 3 minutes, elevating the temperature at a rate of 20° C./min to 210° C. and observing the coming-in and going-out of heat during the process. FIG. 1 shows the obtained measurement results of DSC.

(5) Preparation of a Packed Column for HPLC from the Prepared Separating Agent

A stainless steel-made column having a length of 25 cm and an inner diameter of 1.0 cm was packed with the separating agent having supported the amylose tris[(S)-phenylethyl carbamate] on silica gel prepared in the step (3) above as a packing agent by a slurry packing method to prepare a column for separating enantiomeric isomers.

Example 2

Preparation of an Amylose Tris[(S)-phenylethyl Carbamate]-Supported Separating Agent for Enantiomeric Isomers having an Exothermic Peak before Reaching a Decomposition Temperature (1) Surface Treatment of Silica Gel Surface treatment was performed in the same manner as in Example 1-(1).

(2) Synthesis of Amylose Tris[(S)-phenylethyl Carbamate]

Synthesis was conducted in the same manner as in Example 1-(2).

(3) Supporting of Amylose Tris[(S)-phenylethyl Carbamate] on Silica Gel 10 g of the amylose tris[(S)-phenylethyl carbamate] obtained in the step (2) was dissolved in 100 ml of tetrahydrofuran (THF). About half of the resultant polymer dope was applied uniformly onto 40 g of the silica gel obtained in the step (1). After the completion of the application, THF was distilled off under reduced pressure with heating. Distillation time was set to 30 minutes or less. The remaining half of the polymer dope was uniformly applied to the silica gel in the same manner as described above and THF was distilled off under reduced pressure under the same conditions as the first time to obtain the objective amylose tris[(S)-phenylethyl carbamate]-supported separating agent.

(4) Differential Scanning Calorimetry (DSC) of the Separating Agent Prepared in the Step (3)

Figure 2:
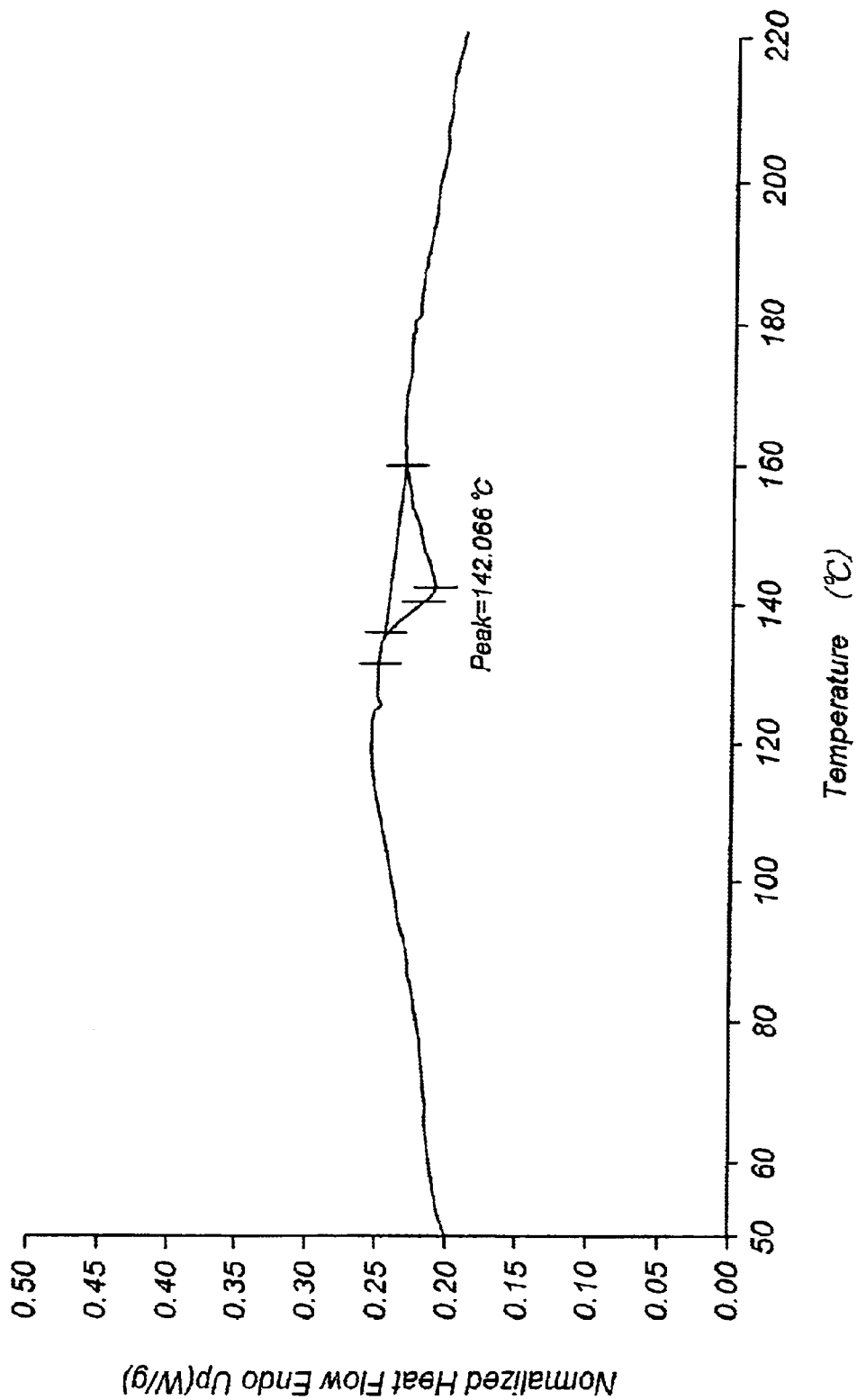
FIG. 2 is a chart illustrating the measurement results of DSC as measured in the step (4) in Example 2 of the present invention.

Differential scanning calorie of the separating agent prepared in the step (3) above was measured by the same technique as in Example 1-(4). FIG. 2 shows the obtained measurement results of DSC.

(5) Preparation of a Packed Column for HPLC from the Prepared Separating Agent

The separating agent having supported the amylose tris [(S)-phenylethyl carbamate] on silica gel prepared in the step (3) above was used as a packing agent to prepare a column for separating enantiomeric isomers in the same manner as in Example 1-(5).

Comparative Example 1

Preparation of an Amylose Tris[(S)-phenylethyl Carbamate]-Supported Separating Agent for Enantiomeric Isomers not having an Exothermic Peak Until Reaching a Decomposition Temperature (1) Surface Treatment of Silica Gel Surface treatment was performed in the same manner as in Example 1-(1).

(2) Synthesis of Amylose Tris[(S)-phenylethyl Carbamate]

Synthesis was conducted in the same manner as in Example 1-(2).

(3) Supporting of Amylose Tris[(S)-phenylethyl Carbamate] on Silica Gel 10 g of the amylose tris[(S)-phenylethyl carbamate] obtained in the step (2) was dissolved in 100 ml of tetrahydrofuran (THF). About half of the resultant polymer dope was applied uniformly onto 40 g of the silica gel described in the step (1). After the completion of the application, THF was distilled off under reduced pressure with heating. Distillation time was set to 60 minutes or more. The remaining half of the polymer dope was uniformly applied to the silica gel in the same manner as described above and THF was distilled off under reduced pressure under the same conditions as the first time to obtain the objective amylose tris[(S)-phenylethyl carbamate]-supported separating agent.

(4) Differential Scanning Calorimetry (DSC) of the Separating Agent Prepared in the Step (3)

Figure 3:
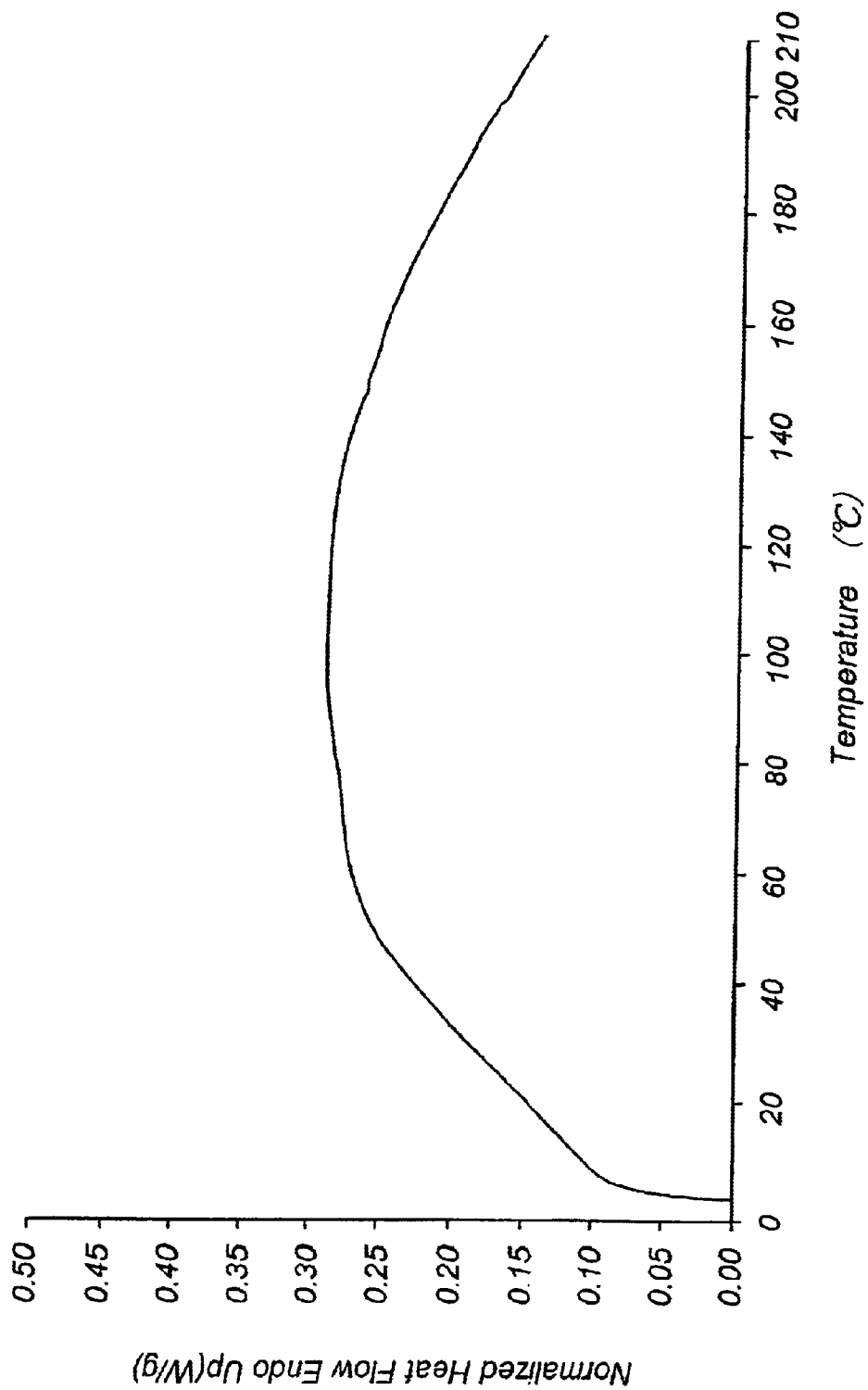
FIG. 3 is a chart illustrating the measurement results of DSC as measured in the step (4) in Comparative Example 1 of the present invention.

Differential scanning calorie of the separating agent prepared in the step (3) above was measured in the same manner as in Example 1-(4) FIG. 3 shows the obtained measurement results of DSC.

(5) Preparation of a Packed Column for HPLC from the Prepared Separating Agent

The separating agent having supported the amylose tris [(S)-phenylethyl carbamate] prepared in the step (3) above on silica gel was used as a packing agent to prepare a column for separating enantiomeric isomers in the same manner as in Example 1-(5).

Application Example

By using HPLC columns for separating enantiomeric isomers packed with the separating agents having supported on silica gels the amylose tris[(S)-phenylethyl carbamates] prepared in Examples 1 and 2 having exothermic peaks, and the separating agent having supported on a silica gel the amylose tris[(S)-phenylethyl carbamate] prepared in Comparative Example 1 having no exothermic peak as packing agents, respectively, enantiomeric resolutions of racemic modifications 1 to 3 of the following formulae were performed by a liquid chromatographic method under the following conditions. Table 1 shows the results obtained.

Racemic modification 1

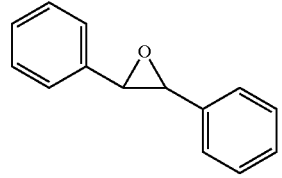

Racemic modification 2

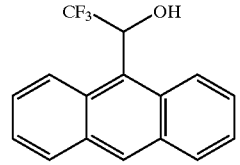

Racemic modification 3

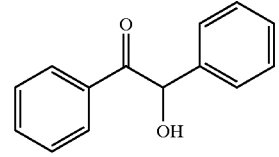

Analysis Conditions

Mobile phase: Hexane/2-propanol=90/10 (v/v)

Flow velocity: 4.7 ml/min

Temperature: 25° C.

Detection: at 254 nm

Equation for calculating the value of separation factor $\alpha$: $\alpha = k_2'/k_1'$ [wherein $k_1'$ and $k_2'$ are each a holding coefficient of enantiomeric isomers and given by the expressions: $k_1' = (t_1 - t_0)/t_0$, and $k_2' = (t_2 - t_0)/t_0$ where $t_1$ and $t_2$ are each an elution time of enantiomeric isomers and $t_0$ is an elution time of tri-tert-butylbenzene]

TABLE 1

|  | Separating agent of Ex. 1 (with an exothermic peak) | Separating agent of Ex. 2 (with an exothermic peak) | Separating agent of Com. Ex. 1 (without exothermic peaks) |
|---|---|---|---|
| Racemic modification 1 | $k_1' = 0.43$<br>$k_2' = 0.66$<br>$\alpha = 1.53$ | $K_1' = 0.53$<br>$K_2' = 0.69$<br>$\alpha = 1.3$ | $k_1' = 0.44$<br>$k_2' = 0.54$<br>$\alpha = 1.22$ |
| Racemic modification 2 | $k_1' = 1.29$<br>$k_2' = 3.14$<br>$\alpha = 2.43$ | $K_1' = 1.39$<br>$K_2' = 3.02$<br>$\alpha = 2.18$ | $k_1' = 1.07$<br>$k_2' = 1.74$<br>$\alpha = 1.63$ |
| Racemic modification 3 | $k_1' = 3.11$<br>$k_2' = 9.17$<br>$\alpha = 2.95$ | $K_1' = 3.44$<br>$K_2' = 6.89$<br>$\alpha = 2$ | $k_1' = 2.86$<br>$k_2' = 4.17$<br>$\alpha = 1.46$ |

What is claimed is:

1. A separating agent for enantiomeric isomers, comprising an enantiomerically active polymer compound supported thereon, wherein the polymer compound has an exothermic peak before a decomposition temperature thereof is reached in a differential calorimetric curve obtained in a process of temperature elevation in differential scanning calorimetry of the separating agent.

2. The separating agent for enantiomeric isomers according to claim 1, wherein the enantiomerically active polymer compound is a polysaccharide derivative.

3. The separating agent for enantiomeric isomers according to claim 1, wherein the enantiomerically active polymer compound is an ester or carbamate derivative of cellulose or amylose.

4. The separating agent for enantiomeric isomers according to claim 1, which is used as a chiral stationary phase for liquid chromatography.

5. The separating agent for enantiomeric isomers according to claim 1, wherein the enantiomerically active polymer compound is amylose tris[(S)-phenylethylcarbamate].

* * * * *